United States Patent
Keller

(10) Patent No.: US 7,914,585 B2
(45) Date of Patent: Mar. 29, 2011

(54) HIP PROSTHESIS INCLUDING A SHAFT TO BE INSERTED INTO THE FEMUR

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 171 days.

(21) Appl. No.: 10/530,211

(22) PCT Filed: Jan. 14, 2004

(86) PCT No.: PCT/EP2004/000225
§ 371 (c)(1),
(2), (4) Date: Apr. 4, 2005

(87) PCT Pub. No.: WO2004/064689
PCT Pub. Date: Aug. 5, 2004

(65) Prior Publication Data
US 2006/0004464 A1    Jan. 5, 2006

(30) Foreign Application Priority Data
Jan. 17, 2003   (EP) .................................... 03001041

(51) Int. Cl.
*A61F 2/36* (2006.01)
(52) U.S. Cl. ............... 623/23.26; 623/23.15; 623/23.31; 623/22.11
(58) Field of Classification Search ................. 623/22.4, 623/22.43, 22.46, 23.26, 23.44, 23.14, 23.15, 623/23.17, 23.21, 22.11, 23.29, 23.31, 23.39
See application file for complete search history.

(56) References Cited

U.S. PATENT DOCUMENTS

| | | | | |
|---|---|---|---|---|
| 4,359,785 A | * | 11/1982 | Niederer | 623/23.15 |
| 4,784,124 A | | 11/1988 | Kaltenbrunner et al. | |
| 5,507,833 A | * | 4/1996 | Bohn | 623/23.3 |
| 5,593,446 A | | 1/1997 | Kuoni | |
| 5,755,811 A | * | 5/1998 | Tanamal et al. | 623/23.35 |
| 6,190,417 B1 | * | 2/2001 | Itoman et al. | 623/23.15 |

FOREIGN PATENT DOCUMENTS

DE    35 05 997 A1    2/1985

(Continued)

OTHER PUBLICATIONS

International Preliminary Report mailed Sep. 2, 2005, directed to counterpart international application.

(Continued)

*Primary Examiner* — David Isabella
*Assistant Examiner* — Suba Ganesan
(74) *Attorney, Agent, or Firm* — Morrison & Foerster LLP

(57) ABSTRACT

A hip prosthesis includes a straight shaft which is to be inserted into the femur, the straight shaft including a proximal part that is configured to be inserted in the metaphyseal region of the femur. The proximal part has, on each of its front and rear faces, at least one projecting fin with a steep medial flank that deviates at least over part of its length away from the longitudinal direction of the shaft. At its top the proximal part is inclined toward the femoral neck. In this way, when the shaft is driven into the bone, the bone substance surrounding the fin is compacted and is able to absorb greater forces. The height of the fin decreases from its medial flank toward its lateral edge.

8 Claims, 1 Drawing Sheet

FOREIGN PATENT DOCUMENTS

| | | |
|---|---|---|
| DE | 44 28 099 C2 | 8/1994 |
| EP | 0 112 435 B1 | 6/1983 |
| EP | 0 159 462 B1 | 1/1985 |
| EP | 0 238 860 A2 | 9/1987 |
| EP | 0 466 638 A1 | 6/1991 |
| EP | 0 682 924 A1 | 11/1995 |
| EP | 0 761 183 A1 | 6/1996 |
| EP | 0 780 106 A2 | 12/1996 |
| EP | 0 821 923 B1 | 7/1997 |
| EP | 1 070 490 A1 | 7/1999 |
| EP | 1 044 665 A2 | 10/2000 |
| FR | 2 549 718 A1 | 2/1985 |
| FR | 2 602 672 A1 | 8/1986 |
| FR | 2 633 509 A1 | 6/1988 |
| FR | 2 668 059 A1 | 10/1990 |
| FR | 2 676 359 A1 | 5/1991 |
| FR | 2 686 789 A1 | 8/1993 |
| FR | 2 791 252 A1 | 9/2000 |
| GB | 2 203 943 A | 11/1988 |
| RU | 2 089 136 C1 | 9/1997 |
| RU | 2 142 757 C1 | 12/1999 |
| RU | 2 255 711 C2 | 1/2004 |
| WO | WO-02/100302 A1 | 12/2002 |

OTHER PUBLICATIONS

Russian Office Action dated Nov. 10, 2006, directed to counterpart Russian Application No. 2005126054/14 (7 pages).

* cited by examiner

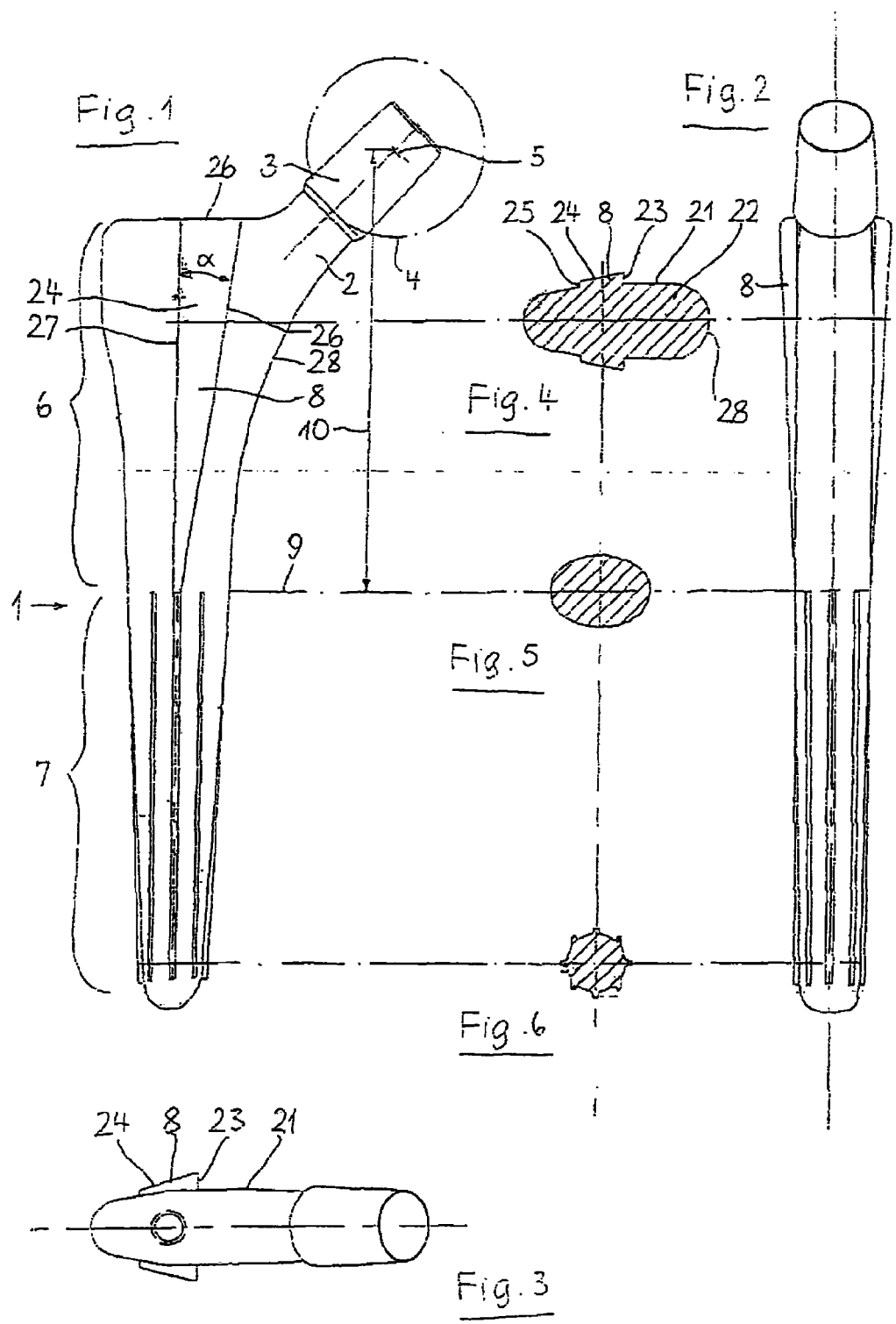

HIP PROSTHESIS INCLUDING A SHAFT TO BE INSERTED INTO THE FEMUR

FIELD AND BACKGROUND OF THE INVENTION

For anchoring a prosthesis shaft in the femur, the conditions in the metaphyseal region are different than those in the diaphyseal region. In the metaphyseal region, i.e. principally in the region above the lesser trochanter, the wide bone space is filled with spongy bone substance in which an artificial receiving channel has to be created to receive a prosthesis shaft. Since the spongy bone substance is soft, the possibilities of force transmission in this region are limited. Below the lesser trochanter, the narrower medullary space is delimited by thick cortical bone, which affords much better conditions for force transmission. Prosthesis shafts have therefore been developed that are especially suitable for anchoring and wedging in this diaphyseal region of the bone (Schneider: Die Totalprothese der Hüfte [The total hip prosthesis], page 214 et seq.). Their reliable anchoring in the diaphyseal region of the bone has the effect that the metaphyseal region of the bone is not loaded. If bone substance is not subjected to loading, it is gradually broken down. This is undesirable.

In prostheses which are primarily to be anchored in the metaphyseal region of the bone, it is known (EP-B-761183; EP-A-780106; EP-A-1070490; EP-B-159462; EP-B-821923; EP-B-112435; DE-C-4428099) to improve the anchoring in the metaphyseal region by means of fins and edges projecting from the ventral and dorsal surfaces of the main body of the prosthesis. These fins require a considerable extent in the lateromedial direction if they are intended for anchoring in bone cement or in a hollow that has been reamed out with the same shape (EP-A-780106; EP-A-1070490; DE-C-4428099). In cementless implantation, however, a particularly stable postoperative fit of the prosthesis in the bone is achieved if fins are used which, in cementless implantation, cut into the bone substance and compress it (EP-B-761183). The hollow space formed in advance in the bone prior to insertion of the prosthesis shaft is then limited to the volume of the main body of the shaft. To ensure that the fins do not burst the bone when the shaft is driven in, they are made narrow and have inclined medial and lateral flanks (EP-B-159462; EP-B-821923; EP-B-761183). This limits their ability to transmit forces.

SUMMARY OF THE INVENTION

The invention relates to the type of prosthesis in which anchoring is sought primarily in the diaphyseal region of the bone. The object of the invention is to counteract the degradation of bone caused by inadequate loading in the metaphyseal region.

The solution according to the invention is that, in accordance with the broad outlines of the invention, the metaphyseal region of the femur is provided with additional force-transmitting means formed by fins. These fins have a particular shape with a steep flank facing in the medial direction. The fin surface facing to the front or rear is accordingly made wider than in the case of the known narrow fins with inclined medial and lateral flanks. However, to ensure that no force arises which could burst the bone when the shaft is being driven into said bone, it is further provided that the fin decreases in height in the lateral direction from the edge delimiting the medial flank. The customary, laterally oriented flank of the fins thus disappears or is reduced to a relatively low height which is at most half the height of the medial flank. This is acceptable because the forces to be transmitted in the lateral direction by the fin are less than the medially directed forces.

The feature to the effect that the medial flank is steep signifies that it forms an almost right angle with the mediolateral plane of the shaft. It should preferably not deviate from this by more than 25°, more preferably by not more than 15°.

At least over part of its length, the medial flank deviates from the longitudinal direction of the shaft and at the top is inclined toward the femoral neck. This shape has the advantage that when the prosthesis is inserted, if the direction of insertion coincides with the longitudinal direction of the prosthesis, the medial flank of the fin, acting like a wedge, compacts the spongy bone substance located in front of it in the insertion direction so that this is able to transmit greater forces. This effect is primarily produced if the angle enclosed by this flank of the fin and the longitudinal direction of the shaft is between 5 and 15°, preferably about 10°.

According to the invention, a corresponding compression on the anterior and posterior faces of the fins can be achieved by the fact that the height of the fins above the respective surface of the main body of the shaft increases from the bottom upward. The fin is thus wedge-shaped in two directions, namely in the first instance toward the medial face and in the second instance toward the anterior or posterior face. The height of the fin can gradually decrease in the lateral direction, i.e. at the side directed away from the steep flank.

The compression of the spongy bone substance by the fins assumes that bone substance was previously present at the place where the fins are located after implantation. If, before insertion of the prosthesis, a channel for receiving the prosthesis shaft is artificially created in the metaphyseal region of the bone, this channel should simply correspond to the cross-sectional shape of the main body of the prosthesis shaft and should therefore not have any bulged-out areas for subsequently receiving the fins. If a rasp is used to form this receiving channel, its shape ought therefore to correspond only to the main body of the shaft, without having means for removing material in the fin area. Alternatively, it is also possible to equip the rasp with fins which correspond to the fins of the prosthesis shaft and are designed for compression of the bone substance without removing material. The above-described compression of the bone substance in the force transmission region of the fins thus comes about through the rasp itself or is prepared partially by the latter.

BRIEF DESCRIPTION OF THE DRAWINGS

The invention is explained in more detail below with reference to the drawing which depicts an advantageous illustrative embodiment and in which:

FIG. 1 shows a front view;
FIG. 2 shows a medial view;
FIG. 3 shows a top view; and
FIGS. 4 to 6 show cross sections through the shaft at the corresponding heights thereof.

DETAILED DESCRIPTION OF THE INVENTION

The prosthesis is composed of a shaft 1, a neck 2 and a cone 3 for attachment of an articulation head 4 whose circumference is indicated by a dot-and-dash line. The shaft is made up of a proximal portion 6 and a distal portion 7. The proximal portion is elongate in cross section in the LM direction, as is shown in FIGS. 4 and 5. It is provided with a pair of fins 8 for transmitting force to the spongy bone substance surrounding the shaft in the epiphyseal region of the femur. The shaft 1 can be seen as a straight shaft. This means that it is of straight configuration and, accordingly, has to be driven into the femur in its longitudinal direction and in the longitudinal direction of the femoral diaphysis.

The transition 9 between the proximal portion and the distal portion of the shaft is arranged so that, in the implanted state, it comes to lie approximately at the lesser trochanter, preferably slightly below the latter, and the distal shaft portion 7 accordingly lies in a region of the medullary canal in which the latter is delimited by thick cortical bone. The transition does not need to be specially marked on the prosthesis. It is determined by the fact that it lies at the point where, in the implanted state, the lesser trochanter or preferably the lower edge of the latter is assumed to be located. It lies generally about 7 to 9 cm deeper than the center point 5 of the articulation head 4, measured according to arrow 10 in the shaft direction.

The distal shaft portion is designed such that it is suitable for anchoring in the diaphyseal region of the femur. To obtain a firm fit, its shaft core is weakly conical and equipped with longitudinal ribs. In this way, the bone substance located in the space between the surface of the shaft core 15 and the cortical margin of the medullary space, is compressed, and, in the process, is held firmly by the ribs. The distal portion can also be configured in another way suitable for primary anchoring of the shaft in the diaphysis of the bone.

The fins 8 rise from the anterior and posterior surfaces 21 of the main body 22 of the shaft. They have a steep flank 23 oriented in the medial direction, and an anterior or posterior surface portion 24 delimited laterally by an edge 25. The surface 24 drops off toward the surface 21 as its distance from the flank 23 increases, so that the fin acquires an approximately triangular or trapezoidal cross-sectional shape, as can be seen in FIGS. 3 and 4. Its height above the surface 21 of the main body 22 is at least twice as great at the medial edge 23 as it is at the lateral edge.

The fins 8 begin at the transition 9 between the proximal portion and the distal portion 7 of the shaft, with a zero height and a minimal width. In the upward direction, they grow uniformly to their maximum height and width, which they reach at the upper end 26. With the longitudinal axis 27 of the shaft, the flank 23 encloses an angle α which, in the illustrative embodiment, is approximately 8°. The height of the flank 23 at the upper end 26 of the shaft is between 2 and 4 mm, preferably about 3 mm. The height of the flank 25 is between zero and half the height of the flank 23. In side view, the flank 25 coincides with the longitudinal axis 27 or extends parallel thereto or at a very small angle thereto.

The cross-sectional surface of the fins increases in a wedge shape from the bottom upward in two directions, namely toward the flank 23 and toward the anterior and posterior surfaces 24. If the hollow formed for receiving the prosthesis shaft in the metaphyseal, spongy region of the femur is identical in cross section to the main body 22 of the shaft, then the fins 8, when the shaft is driven in, displace the spongy substance located there and compact it. It is thus made more suitable for transmitting forces. The dropping-away of the fin from the medial edge to the lateral edge has the further advantage that the space available in the metaphysis of the bone can be better utilized for a large shaft design.

The illustrative embodiment shows a linear course of the fins 8. Their wedge shape, however, can also have a nonlinear course.

Although the prosthesis is intended for primary anchoring in the diaphysis, the flanks 23 and the other surfaces 28 of the prosthesis shaft that are oriented in the medial direction, contribute to the transmission of forces in the metaphyseal region too. The metaphysis of the bone thus participates in the transmission of force. The danger of its degeneration is thus reduced. The long-term secure hold of the prosthesis in the bone is improved.

The invention claimed is:

1. A hip prosthesis configured for cementless implantation comprising a shaft configured to be inserted into a femur and a femoral neck extending medially relative to an implanted position of the prosthesis in the femur, the shaft having a proximal part configured to be inserted in a metaphyseal region of the femur and a distal part configured to be inserted into a diaphyseal region of the femur, the proximal part comprising fins that project from front and rear faces of the proximal part, each fin extending from a distal end of the proximal part to a proximal end of the proximal part and having a steep medial flank oriented in a medial direction relative to the implanted position, the steep medial flank enclosing an angle between 5° and 15° with respect to a longitudinal axis of the shaft, the width of the fins increasing from the distal end to the proximal end of the proximal part, the height of the fins decreasing in a lateral direction, relative to the implanted position and perpendicular to the longitudinal axis of the shaft, from the medial edge, the distal part comprising diaphyseal anchoring projections.

2. The prosthesis as claimed in claim 1, wherein the fins extend rectilinearly.

3. The prosthesis as claimed in claim 1 or 2, wherein the height of the fins above the surface of the shaft increases from the distal end to the proximal end of the proximal part.

4. The prosthesis as claimed in claim 3, wherein the height of the lateral edge of the fins is not greater than half the height of the medial edge.

5. The prosthesis as claimed in claim 3, further comprising a device for anchoring the endoprosthesis to a diaphysis.

6. The prosthesis as claimed in claim 1 or 2, wherein the height of the lateral edge of the fins is not greater than half the height of the medial edge.

7. The prosthesis as claimed in claim 6, further comprising a device for anchoring the endoprosthesis to a diaphysis.

8. The prosthesis as claimed in claim 1 or 2, further comprising a device for anchoring the endoprosthesis to a diaphysis.

* * * * *